United States Patent
Nguyen et al.

(10) Patent No.: US 6,926,730 B1
(45) Date of Patent: Aug. 9, 2005

(54) MINIMALLY INVASIVE VALVE REPAIR PROCEDURE AND APPARATUS

(75) Inventors: John D. Nguyen, San Jose, CA (US); Laurent Schaller, Los Altos, CA (US); Art Hill, San Francisco, CA (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 09/686,004

(22) Filed: Oct. 10, 2000

(51) Int. Cl.$^7$ .............................................. A61B 17/08
(52) U.S. Cl. ..................................... 606/213; 606/151
(58) Field of Search ................................ 606/151, 157, 606/213, 139, 228, 227, 221, 225, 233, 232, 217, 218, 127, 203

(56) References Cited

U.S. PATENT DOCUMENTS

| | | | |
|---|---|---|---|
| 3,802,438 A | | 4/1974 | Wolvek |
| 4,006,747 A | | 2/1977 | Kronenthal et al. |
| 4,396,139 A | | 8/1983 | Hall et al. |
| 5,002,563 A | * | 3/1991 | Pyka et al. .................. 606/222 |
| 5,127,413 A | * | 7/1992 | Ebert .......................... 128/898 |
| 5,217,027 A | * | 6/1993 | Hermens ..................... 607/126 |
| 5,304,204 A | | 4/1994 | Bregen |
| 5,366,479 A | | 11/1994 | McGarry et al. |
| 5,450,860 A | | 9/1995 | O'Connor |
| 5,454,834 A | * | 10/1995 | Boebel et al. ............... 606/228 |
| 5,500,000 A | | 3/1996 | Feagin et al. |
| 5,628,757 A | * | 5/1997 | Hasson ........................ 606/139 |
| 5,665,109 A | * | 9/1997 | Yoon ........................... 606/232 |

(Continued)

FOREIGN PATENT DOCUMENTS

WO WO 99/62406 A2 12/1999
WO WO 99/62409 A1 12/1999

(Continued)

OTHER PUBLICATIONS

Maisano, F. et al. The Double Orifice Technique as a Standardized Approach to Treat Mitral Regurgitation Due to Severe Myxomatous Disease: Surgical Technique (European Journal of Cardiothoracic Surgery, vol. 17 (2000) 201–205).

(Continued)

*Primary Examiner*—(Jackie) Tan-Uyen T. Ho
(74) *Attorney, Agent, or Firm*—Tom Berry; Jeffrey J. Hohenshell (57) ABSTRACT

A clip of a self-closing type is used for valve repair. The clip is generally U-shaped with two end points separated from each other when it is constrained to be in an open configuration, but tends to coil up to assume its natural closed configuration if the constraint is removed. At least one end point is connected through a suture to a tissue-penetrating needle. A needle holder has an outer tube and an inner member which has a slit at the front and is slidable inside the outer tube. They are designed such that the slit can grab the needle tightly or release it as the inner member is moved backward or forward with respect to the outer tube. With the needle secured at the front, the needle holder is passed through a cannula inserted through an incision and the needle penetrates the leaflets such that the clip can be positioned with its end points hooked to the pair of leaflets to be stitched together. If the clip is released from the suture thereafter, it tends to coil up, reducing the distance between the end points and pulling the leaflets together. A double-arm clip assembly with each of the end points of the clip attached through a suture to a separate needle may be similarly used for valve repair. Such a double-arm clip assembly may contain two of such clips mutually connected by means of a flexible connector such that two leaflets are held together by the connector, with the two clips each anchored to a corresponding one of the leaflets.

20 Claims, 6 Drawing Sheets

U.S. PATENT DOCUMENTS

| | | | |
|---|---|---|---|
| 5,695,505 A | 12/1997 | Yoon | |
| 5,715,987 A | 2/1998 | Kelley et al. | |
| 5,725,542 A | 3/1998 | Yoon | |
| 5,871,528 A | * 2/1999 | Camps et al. | 600/374 |
| 5,908,428 A | 6/1999 | Scirica et al. | |
| 5,961,539 A | 10/1999 | Northrup, III et al. | |
| 5,972,024 A | * 10/1999 | Northrup et al. | 606/151 |
| 5,976,159 A | 11/1999 | Bolduc et al. | |
| 5,984,917 A | * 11/1999 | Fleischman et al. | 606/139 |
| 5,984,959 A | 11/1999 | Robertson et al. | |
| 5,989,268 A | 11/1999 | Pugsley, Jr. et al. | |
| 6,074,401 A | 6/2000 | Gardiner et al. | |
| 6,113,611 A | 9/2000 | Allen et al. | |
| 6,165,183 A | 12/2000 | Kuehn et al. | |
| 6,193,733 B1 | 2/2001 | Adams | |
| 6,221,083 B1 | * 4/2001 | Mayer | 606/139 |
| 6,269,819 B1 | 8/2001 | Oz et al. | |
| 6,514,265 B2 | 2/2003 | Ho et al. | |
| 6,551,332 B1 | 4/2003 | Nguyen et al. | |
| 6,607,541 B1 | 8/2003 | Gardiner et al. | |
| 6,613,059 B2 | 9/2003 | Schaller et al. | |
| 6,641,593 B1 | 11/2003 | Schaller et al. | |

FOREIGN PATENT DOCUMENTS

| | | |
|---|---|---|
| WO | WO 00/03759 A2 | 1/2000 |
| WO | WO 00/64381 A2 | 11/2000 |
| WO | WO 01/26557 A1 | 4/2001 |
| WO | WO 01/26586 A1 | 4/2001 |
| WO | WO 01/28432 A1 | 4/2001 |

OTHER PUBLICATIONS

Chitwood Jr., W. Randolph. Mitral Valve Repair: Ischemic (Mastery of Cardiothoracic Surgery, Lippencott–Raven Publishers (1998) 309–321).

Written Opinion PCT/US01/31709 of Nov. 12, 2002.

International Search Report PCT/US01/31709 of Jan. 17, 2002.

* cited by examiner

MINIMALLY INVASIVE VALVE REPAIR PROCEDURE AND APPARATUS

BACKGROUND OF THE INVENTION

This invention relates to methods and apparatus for minimally invasive valve repair and more particularly to minimally invasive methods and apparatus for reducing the valve orifice.

Valve repair is currentnly done in open surgical procedures as described, for example, by F. Maisano, et al. in their article entitled "The double-orifice technique as a standardized approach to treat mitral regurgitation due to severe myxomatous disease" which appeared in European Journal of Cardio-thoracic Surgery, Vol. 17 (2000) 201–205. Cumbersome suture management, knot tying pain and long recovery time are inherent to such open surgical procedures. It now goes without saying that minimally invasive surgery is the preferred procedure, having allowed surgeons to perform procedures with less pain and disability than open surgical procedures. Tissue-connector apparatus and methods usable in such minimally invasive surgery procedures have recently been disclosed in U.S. patent application Ser. Nos. 09/089,884, now U.S. Pat. No. 6,607,541, and 09/090,305, now U.S. Pat. No. 6,641,593, both filed Jun. 3, 1998 and Ser. Nos. 09/259,705, now U.S. Pat. No. 6,514,265, and 09/260,623, now U.S. Pat. No. 6,613,059, both filed Mar. 1, 2000.

It is therefore a general object of this invention to provide improved minimally invasive methods and apparatus for coaptation of leaflets in the case of regurgitation to reduce the annular orifice.

It is a more specific object of this invention to provide such improved minimally invasive methods and apparatus using a tissue-connector apparatus disclosed in aforementioned U.S. patent applications.

SUMMARY OF THE INVENTION

Methods and apparatus embodying this invention with which the above and other objects can be accomplished are characterized as using a clip of a self-closing type as a tissue connector to capture leaflets and secure them together. Such a clip is typically U-shaped, having two end points, when it is constrained to be in an open configuration but is made of a wire of a shape memory material such that it tends to coil up to assume its natural closed configuration. Thus, if such a clip is placed between a pair of valve leaflets to be repaired, having each of its end points penetrating and completely passing through a different one of the leaflets while being constrained to be in its open configuration, and if the constraint which has been keeping the clip in its open configuration is then removed, it naturally tends to coil up, although it will not come to assume its natural closed configuration because it is hooked to the leaflets, tending nevertheless to reduce the distance of separation between its two end points. This has the effect of holding the leaflets together.

Such a clip may be deployed in the form of a clip assembly, having at least one of the end points of the clip connected to a tissue-piecing needle through a flexible member such as a suture and a release mechanism by which the clip can be easily released. The needle is attached to the front end of a needle-holder and passed through a cannula inserted through an incision towards the valve leaflets to be repaired. The needle-holder, according to a preferred embodiment of the invention, is formed with an outer tube and an inner member which is slidable inside the outer tube and is designed such that as the inner member is pushed forward against the biasing force of a spring contained in the outer tube, a slit which is provided at the front end becomes wider for accepting the needle therein but as the inner member is allowed to move to a backward position, the slit becomes narrower and grips the needle tightly.

BRIEF DESCRIPTION OF THE DRAWINGS

The accompanying drawings, which are incorporated in and form a part of this specification, illustrate embodiments of the invention and, together with the description, serve to explain the principles of the invention. In the drawings.

Throughout herein like components are indicated by the same numerals even where they are components of different assemblies and may not necessarily described repetitiously.

The schematic drawings are intended to be indeed schematic and only to show the basic concepts of the invention, not necessarily representing realistic views, for example, with realistic relative sizes of body components and apparatus components.

DETAILED DESCRIPTION OF THE INVENTION

Figure 1:
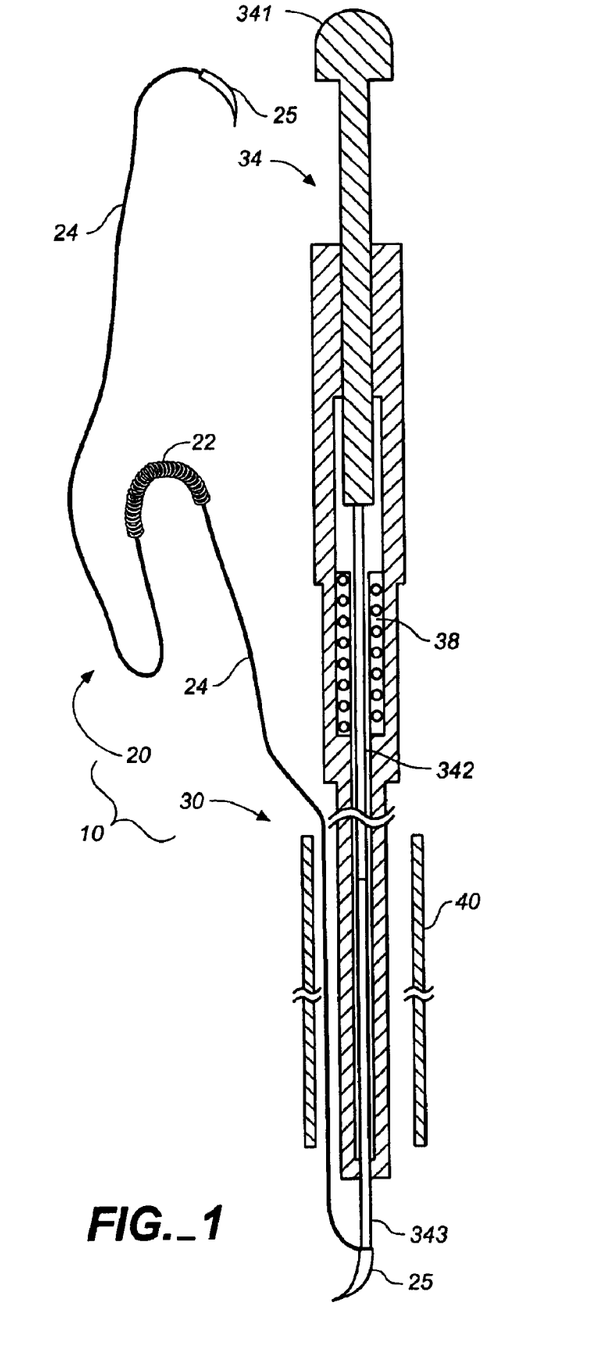
FIG. 1 is a schematic view of a tissue-connector apparatus embodying this invention when it is about to be used, its double-arm clip assembly being shown as a diagonal view and its needle holder being shown as a sectional side view.

The invention is described next by way of examples. FIG. 1 shows schematically a tissue-connector apparatus 10 embodying this invention for a minimally invasive procedure. Described briefly, the apparatus 10 consists of a clip assembly 20 and a needle holder 30, which will be described next sequentially in detail.

The clip assembly 20 according to this embodiment may be referred to as the double-arm clip assembly, characterized as having a clip 22 of a self-closing type with two end points each connected through a flexible member 24 such as a suture to a tissue penetrating needle 25 (as disclosed, for example, in aforementioned U.S. patent application Ser. Nos. 09/259,705, now U.S. Pat. No. 6,514,265, and 09/260,623, now U.S. Pat. No. 6,613,059, both filed Mar. 1, 2000, both of which applications are herein incorporated by reference). Each of the needles 25 has a tissue-piercing sharp point and is connected to a corresponding one of the flexible members 24. As shown more clearly in FIG. 2, the two end points of the clip 22 are each provided with and directly connected to a release mechanism 23 such that it can be released easily from the flexible members 24 and from being constrained to remain it its generally U-shaped open configuration.

Figure 2:
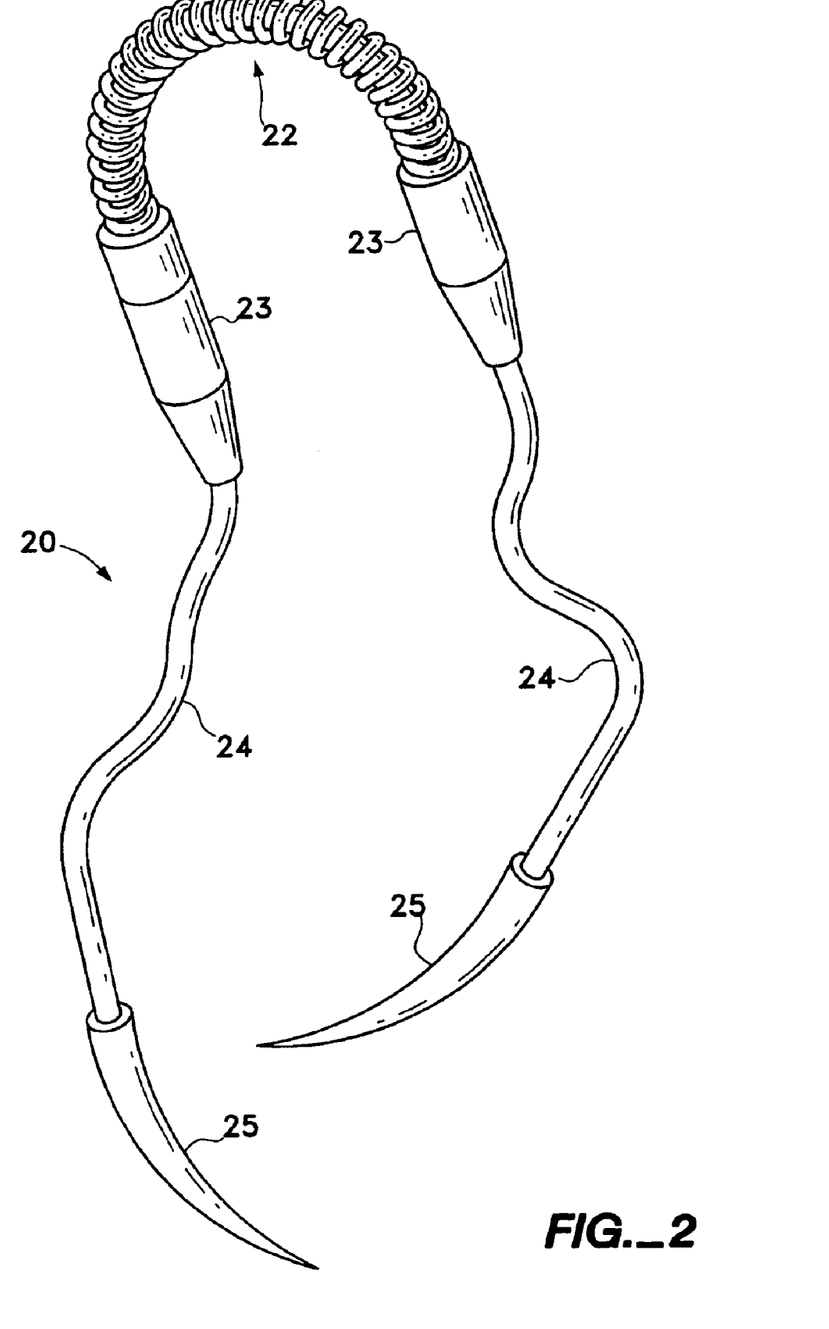
FIG. 2 is an enlarged external view of the double-arm clip assembly of FIG. 1.

The clip 22, or a surgical fastener, of the so-called self-closing type may be one disclosed in aforementioned U.S. patent application Ser. Nos. 09/089,884, now U.S. Pat. No. 6,607,541, and 09/090,305, now U.S. Pat. No. 6,641,593, both filed Jun. 3, 1998 (herein said Ser. Nos. 09/089,884 and 09/090,305 applications also incorporated by reference), as well as in aforementioned U.S. patent application Ser. Nos. 09/259,705, now U.S. Pat. No. 6,514,265, and 09/260,623, now U.S. Pat. No. 6,613,059, characterized as having two end points, being generally U-shaped when in an open configuration (as shown in FIGS. 1 and 2), being naturally in a closed configuration (state or condition) and being elastic (or pseudoelastic, but herein broadly characterized as being "elastic") so as to tend to return to the closed configuration by reducing the separation distance between its end points when forced into an open configuration. As disclosed in aforementioned U.S. patent application Ser. Nos. 09/089,884, now U.S. Pat. No. 6,607,541, and 09/090,305, now U.S. Pat. No. 6,641,593, such a clip 22 may comprise a deformable wire made of a shape memory alloy such as a nickel titanium based alloy (nitinol). It is also known that the alloy may include additional elements, depending on the desired yield strength of the material or the temperature at which particular pseudoelastic or shape transformation characteristics occur. When the clip 22 is in its closed configuration (not shown) with no external restraining force thereupon, it may be in a completely closed loop with its end points in a side-by-side or overlapping orientation, the wire being looped by more than 360°. The diameter of the wire for the clip 22 and the diameter of the loop when it is in the closed configuration may be selected, depending on the application, and do not limit the scope of the invention.

Figure 3:
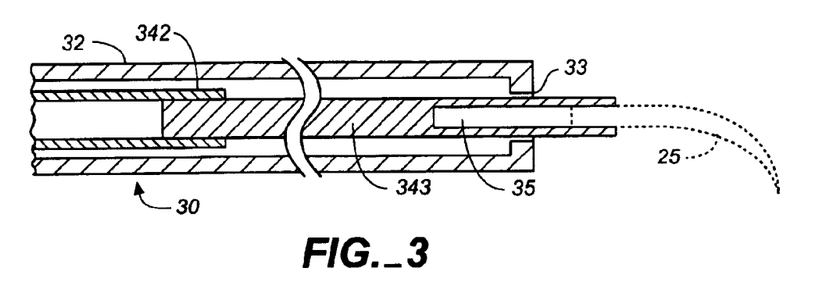
FIG. 3 is an enlarged sectional view of a portion of the needle holder near its front end.

The needle holder 30 consists essentially of a hollow outer tube 32, an inner member 34 and a spring 38, as shown in FIG. 1. The outer tube 32 is elongated, defining a longitudinal direction. The inner member 34 is also longitudinally elongated and is adapted to slide longitudinally inside the outer tube 32 and to releasable grab the needles 25, one at a time. According to the embodiment shown in FIG. 1, the inner member 34 is comprised of a knob 341 at its proximal end, a conjunction tube 342 in the middle and a needle-holding tube 343 in front. The conjunction tube 342 and the needle holding tube 343 are laser-welded together. A threaded adapter is laser-welded to the proximal end of the conjunction tube 342 for allowing the knob 341 to be screwed thereonto after the spring 38 is inserted inside the outer tube 32 such that, once the needle holder 30 is thus assembled, the knob 341, the conjunction tube 342 and the needle-holding tube 343 will move together as a single unit. The front end of the needle-holding tube 343 is provided with a longitudinally elongated slit 35 for holding the needle 25, and the outer tube 32 has a front opening 33, as shown more clearly in FIG. 3. The needle-holding tube 343 with the slit 35 and the front opening 33 of the outer tube 32 are so designed that the slit 35 will open and become sufficiently wide in front as the inner member 34 is pushed forward through the outer tube 32 for accepting a needle 25 (shown by broken lines in FIG. 3) therein and that the opening of the slit 35 tends to become smaller as the inner member 34 is moved backwards through the outer tube 32 so as to retract the needle-holding tube 343 through the front opening 33 of the outer tube 32, causing the needle-holding tube 343 to securely grab the needle 25 once accepted. The spring 38 is disposed inside the outer tube 32 so as to provide a backward biasing force on the inner member 34. In other words, the inner member 34 is normally in a backward position inside the outer tube 32 under the influence of the backward biasing force of the spring 38 thereon. As the user pushes the inner member 34 forward by operating the knob 341 against aforementioned backward biasing force of the spring, the front part of the needle-holding tube 343 protrudes farther outward from the front opening 33 of the outer tube 32 and the slit 35 opens wider, its front opening becoming wide enough to accept the back part of a needle (away from its tissue-piercing sharp point). If the user then releases the force being applied to the knob 341 after the back part of the needle 25 has been accepted inside the slit 35, the backward biasing force by the spring pushes the inner member 34 backward, reducing the length of the needle-holding tube 343 outside the front opening 33 of the outer tube 32. This has the effect of reducing the opening of the slit 35 and hence of having the needle 25 firmly gripped by the needle holder 30. In summary, the user pushes the knob 341 forward to accept the needle 25 and releases the force on the knob 341 to firmly grab it. When a needle is already being held by the needle holder 30, the user has only to push the knob 341 to release it.

A valve repair procedure embodying this invention, such as for reducing the valve orifice by using the apparatus described above, will be described next.

Figure 4A:
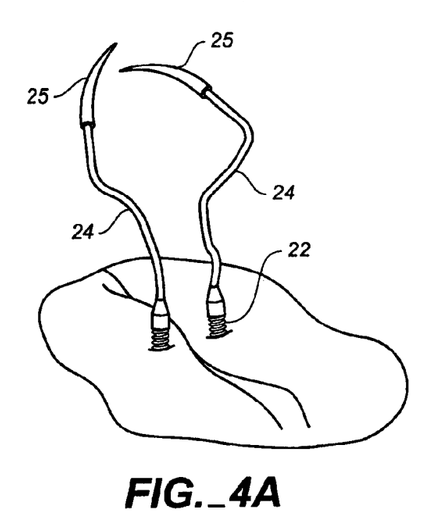
FIG. 4A is a schematic diagonal view of the clip assembly of FIGS. 1 and 2 being used in a valve repair procedure embodying this invention.
Figure 4B:
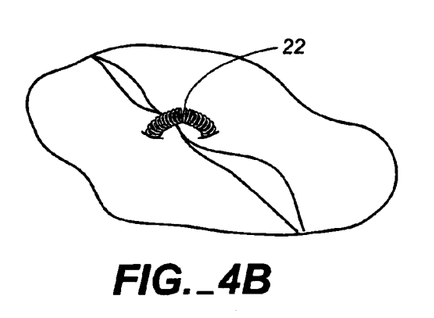
FIG. 4B is another schematic diagonal view of the clip of FIG. 4A after it has been released.

To access a mitral valve, a small incision is made on the appendage of the left atrium. One of the needles 25 of the clip assembly 20 is grabbed by the needle holder 30, as shown in FIG. 1, by pushing the knob 341 forward to accept the needle 25 and then releasing it to firmly attach the needle 25 to the needle holder 30, as described above. A cannula is inserted into the incision. FIG. 1 shows the cannula schematically at 40 but the patient's body part are omitted from FIG. 1. With an aid of an ultrasound machine (not shown), the needle holder 30 is passed through the cannula 40 towards the leaflets, and the needle 25 held by the needle holder 30 is caused to penetrate and be completely pulled through one of the leaflets. Thereafter, the knob 341 is pushed forward to release the needle 25. The knob 341 is pushed forward again to grab the same needle 25 from the other side of the leaflet to secure the needle 25 on the leaflet. Thereafter, the needle 25 is released, the needle holder 30 is pulled out of the cannula 40 and the other of the needles 25 of the double-arm clip assembly 20 is similarly grabbed by its needle holder 30. The same procedure as described above is repeated to cause the second needle 25 of the clip assembly 20 to penetrate and be completely pulled through and be secured to the other of the leaflets. The needles 25 are pulled, together with the flexible members 24 attached thereto, until the clip 22 comes to span the leaflets, as shown in FIG. 4A. Thereafter, the release mechanisms 23 are squeezed by an instrument such as the needle holder 30 itself to release the clip 22 from the flexible members 24. Free of constraints, the clip 22 now tends to return to its natural closed configuration, reducing the distance separating its two end points. This has the effect of tightly bringing the leaflets together, as shown in FIG. 4B, thereby reducing the valve orifice.

The invention was described above by way of only one example but this example is not intended to limit the scope of the invention. Many modifications and variations are possible within the scope of the invention. For example, although the use of a clip assembly having two needles each connected to a corresponding one of the two end points of a generally U-shaped clip was disclosed, use may be made under certain circumstances of a simpler single-arm clip assembly 20' shown in FIG. 5 and described, for example, in aforementioned U.S. patent applications Ser. Nos. 09/089,884, now U.S. Pat. No. 6,607,541, and 09/090,305, having only one needle 25 attached through a flexible member 24 and a release mechanism 23 to one of the two end points of a clip 22'. Such a single-arm clip assembly 20' may be used similarly, as described above in connection with the double-arm clip assembly 20 shown in FIGS. 1 and 2, except that the clip 22' is provided with a stopper 26 at the other of its two end points not connected to the flexible member 24 for keeping the clip 22' in its generally U-shaped open configuration. After the needle 25 is caused to penetrate both leaflets, as shown in FIG. 6, the clip 22' can be caused to pull the two leaflets together as the flexible member 24 is pulled, the stopper 26 serving to locate the clip 22' across the leaflets.

Figure 5:
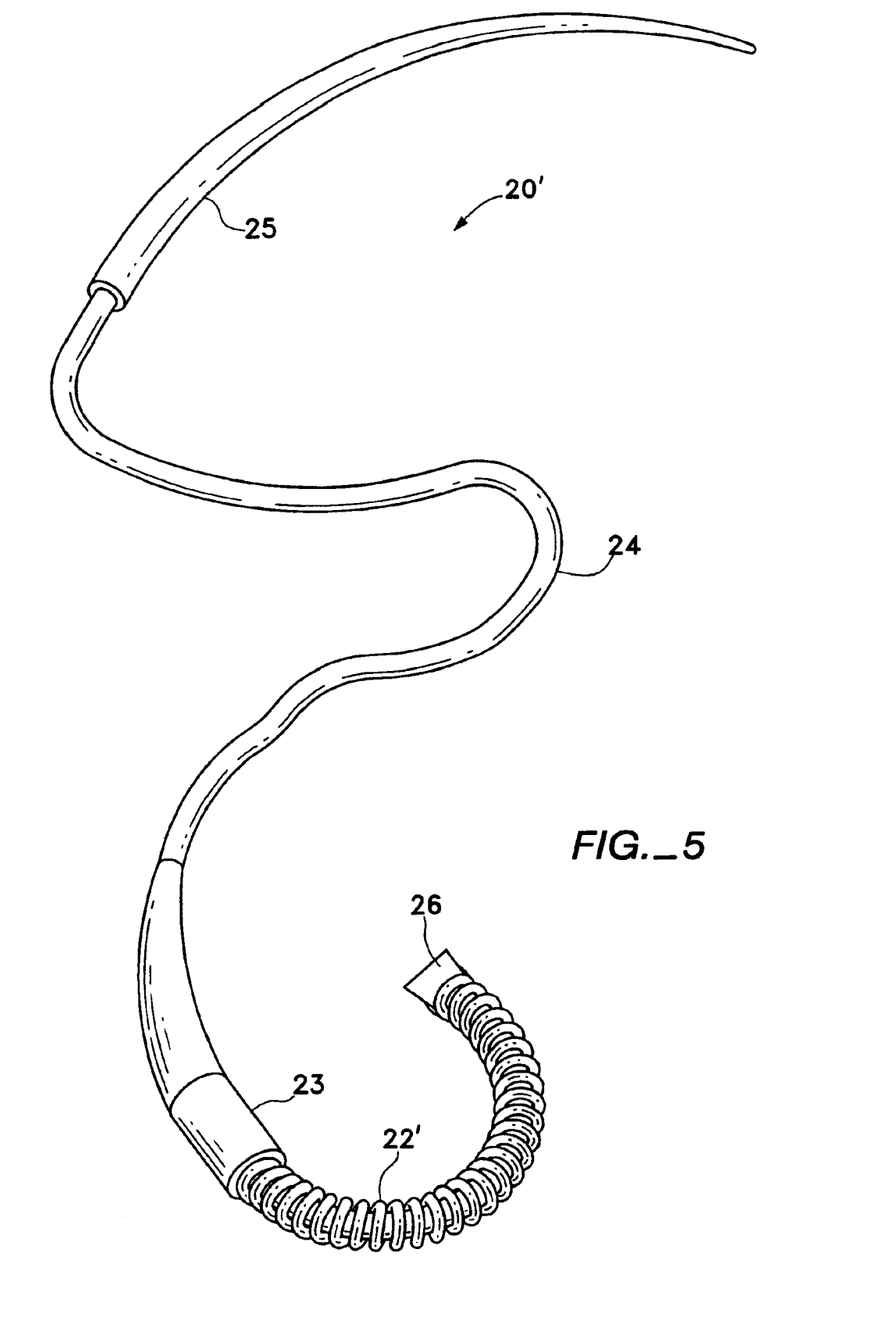
FIG. 5 is an external view of a single-arm clip assembly which may be used in a method of minimally invasive valve repair embodying this invention.
Figure 6:
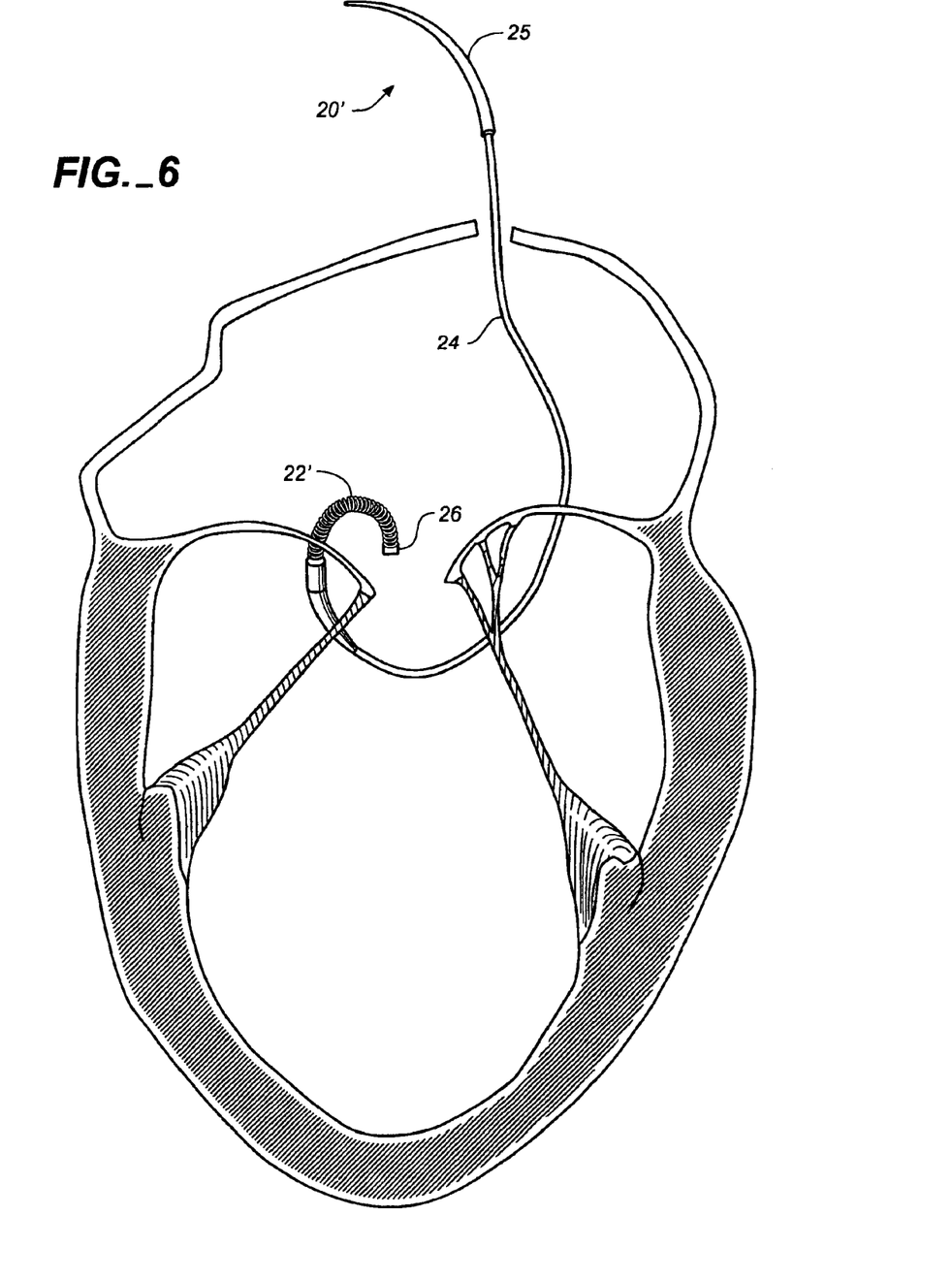
FIG. 6 is a schematic sectional view for showing a method of valve repair embodying this invention by using the single-arm clip assembly of FIG. 5.
Figure 7:
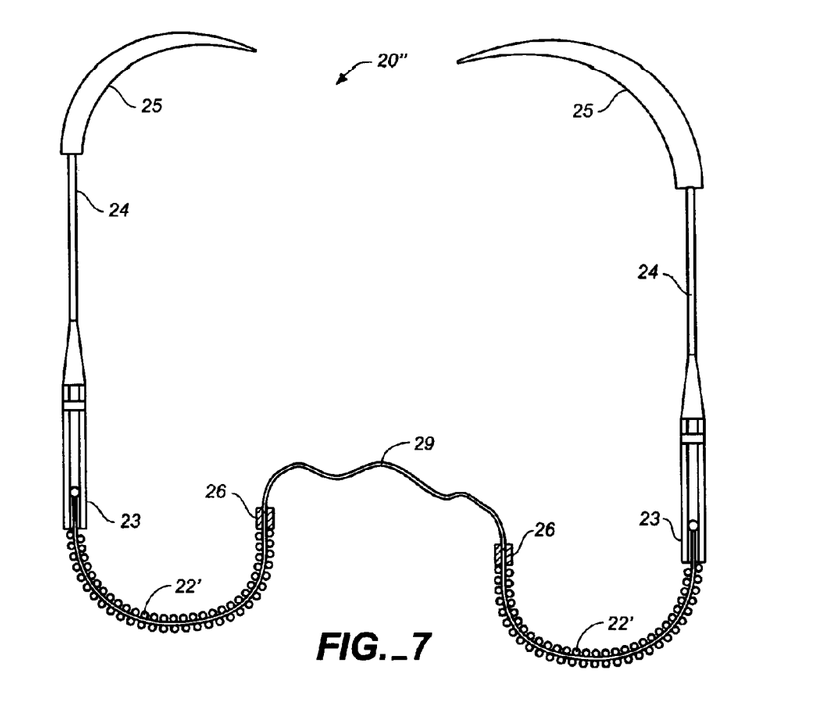
FIG. 7 is another clip assembly embodying this invention.

FIG. 7 shows still another clip assembly 20" embodying this invention, indicating like components by the same numerals as used in FIGS. 2 and 5. This clip assembly 20" is characterized as having not only two tissue penetrating needles 25 each connected to a flexible member 24 but also two self-closing clips 22' as shown in and explained with reference to FIG. 5, each having a stopper 26 at one end point for keeping the clip 22' in a generally U-shaped open configuration and the other end point being connected to a corresponding one of the flexible members 24 through a release mechanism 23 for separating the clip 22' from the flexible member 24 and thereby releasing the clip 22' from remaining in its open configuration. These two clips 22' are connected through their stoppers 26 by another flexible member 29 which may be a suture or a metal wire.

Figure 8A:
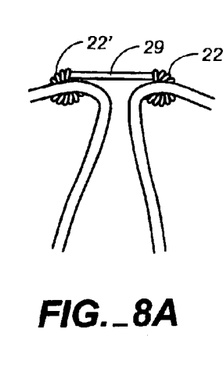
FIG. 8A is a schematic sectional view of leaflets repaired by a clip assembly of FIG. 7.
Figure 8B:
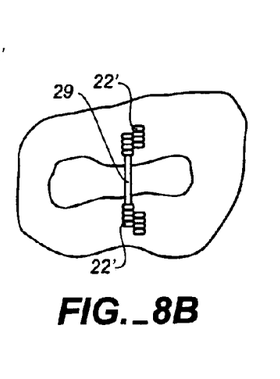
FIG. 8B is a top view of the leaflets of FIG. 8A.
Figure 8C:
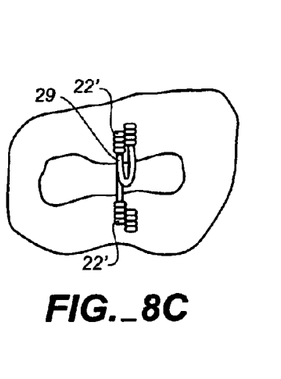
FIG. 8C is a top view of leaflets repaired in an alternative manner.

A clip assembly 22' thus structured may be used in a valve repair procedure, for example, by penetrating a leaflet tissue with one of the needles 25, causing it to come up and out at another position in a manner of ordinary stitching, pulling the associated flexible member 24 until the clip 22' connected thereto penetrates the leaflet tissue partially such that the end point of this clip 22' on the side of the release mechanism 23 penetrates the tissue and reappears on the surface while the other end point on the side of the stopped 26 does not penetrate the tissue, and doing the same with the other needle 25 on the leaflet on the opposite side of the valve opening. After the release mechanisms 23 on both clips 22' are pressed, as described above, to release the clips 22' from the needles 25, each clip 22' tends to coil up, getting firmly attached to the respective leaflet, the flexible member 29 therebetween holding the leaflets together, as shown in FIGS. 8A and 8B. In other words, it is the flexible member 29 between the two. clips 22' that holds the leaflets together. As an alternative procedure, the needles 25 may be operated such that the connecting flexible member 29 makes a loop between the leaflets, as shown in FIG. SC.

Although the clips 22 and 22', when constrained to an open configuration before they are released from the flexible member 24, are described as being generally U-shaped, this description is intended to be interpreted broadly. As should be clear from the intended function of the clips 22 and 22', their open configuration may took more like a C or a J than a U. The release mechanisms 23, described above as serving to release the connection between the clip 22 or 22' and the flexible members 24 and to release the clip 22 or 22' from its forced open configuration, may be structured as disclosed in aforementioned U.S. patent application Ser. No. 09/260,623, now U.S. Pat. No. 6,613,059, but their structure is not intended to limit the scope of the invention.

In summary, the disclosure is intended to be interpreted broadly. Although the invention has been described as being addressed to a method and an apparatus for valve repair, a person skilled in the art will immediately realize that the method and apparatus of this invention as described above can be used for holding two tissue parts close together, not being limited to valve leaflets. The scope of this invention, therefore, is to be understood as including methods of and apparatus for holding two tissue parts close together.

What is claimed is:

1. Apparatus for minimally invasive valve repair, said apparatus comprising:
    a tissue penetrating needle, a flexible member, and a clip, and tissue penetrating needle being connected through said flexible member to said clip, said clip having two end points which are separated from each other when said clip is in an open configuration and tending to return to a naturally closed configuration by reducing distance between said end points when in said open configuration;
    a needle holder including an outer tube and an inner member which has a front end adapted to grab said needle and is slidable inside said outer tube;
    a second needle and a second flexible member coupled to said second needle, wherein each flexible member is connected to one of said two end points of said clip; and
    a pair of release mechanisms each being directly attached to one of said end points of said clip to releasably connect said flexible members to said clip.

2. The apparatus of claim 1 wherein said needle holder further includes a spring which is disposed inside said outer tube and serves to apply a biasing force on said inner member backward away from said front end.

3. The apparatus of claim 2 wherein said front end of said inner member has a slit for accepting and grabbing said needle therein.

4. The apparatus of claim 3 wherein said outer tube, said inner member and said slit are designed such that said slit opens wide enough to accept said needle therein and to release said needle therefrom when said inner member is pushed forward against said biasing force and said slit becomes narrower and firmly grips said needle therein when said inner member is moved backward.

5. The apparatus of claim 1 wherein said clip is generally U-shaped when in said open configuration.

6. The apparatus of claim 1 wherein said clip comprises a wire made of shape memory material.

7. The apparatus of claim 1 wherein said clip in said closed configuration is looped by more than 360°.

8. A minimally invasive method of holding two valve leaflets in a patient together, said method comprising:
    providing a clip having two end points which are separated from each other when said clip is in an open configuration and tending to return to a naturally closed configuration by reducing distance between said end points when in said open configuration;
    placing said clip across. two valve leaflets in a patient such that said two end points each penetrate completely a different one of the two leaflets while said clip is in said open configuration; and
    allowing said clip to tend to return to said closed configuration, whereby the two valve leaflets are held together by said clip, wherein said two end points of said clip are each detachably attached to a tissue penetrating needle through a flexible member, and wherein placing said clip comprises penetrating and completely pulling one of the needles through one of said two valve leaflets and the other of the needles through the other of the two valve leaflets.

9. The method of claim 8 further comprising:

releasably grabbing one of said needles by a needle holder;

inserting a cannula through an incision towards the valve leaflets;

advancing said needle holder through said cannula with said one needle grabbed thereby;

operating said needle holder to cause said one needle to penetrate and be completely pulled through said one of said two valve leaflets from one side to the other side;

thereafter releasing said needle from said needle holder;

thereafter grabbing and pulling said needle again by said needle holder from the other side of said one of said two valve leaflets;

thereafter releasably grabbing the other of said needles by said needle holder, advancing said needle holder through said cannula with the other needle grabbed thereby, operating said needle holder to cause the other needle to penetrate and be completely pulled through the other valve leaflet from one side to the other side thereof;

thereafter situating said clip on both of said two valve leaflets; and thereafter detaching said clip from the needles.

10. The method of claim 9 wherein said needle holder includes an outer tube and an inner member which has a front end adapted to releasably grab said needle and is slidable inside said outer tube.

11. The method of claim 10 wherein said needle holder further includes a spring which is disposed inside said outer tube and serves to apply a force on said inner member backward away from said front end.

12. The method of claim 8 wherein said clip comprises a wire made of shape memory material.

13. The method of claim 8 wherein said clip in said closed configuration is looped by more than 360°.

14. A minimally invasive method of holding two valve leaflets in a patient together, said method comprising:

providing a clip having two end points which are separated from each other when said clip is in an open configuration and tending to return to a naturally closed configuration by reducing distance between said end points when in said open configuration;

placing said clip across two valve leaflets in a patient while said clip is in said open configuration; and allowing said clip to tend to return to said closed configuration, whereby the two valve leaflets are held together by said clip, wherein one of said two end points of said clip is detachably attached to a tissue penetrating needle through a flexible member, and wherein placing said clip comprises penetrating and completely pulling said needle through one of the two valve leaflets and thereafter the other of the two valve leaflets.

15. The method of claim 14 wherein said clip comprises a wire made of shape memory material.

16. The method of claim 14 wherein said clip in said closed configuration is looped by more than 360°.

17. A minimally invasive method of holding two valve leaflets in a patient together comprising:

providing a clip having an open configuration, a closed configuration to which said clip tends to return, first and second ends which are separated from one other when the clip is in the open configuration, and a tissue penetrating needle detachably attached to the first end of the clip through a flexible member;

positioning the clip to span two valve leaflets in a patient while the clip is in the open configuration by penetrating and completely passing the needle through one of the two valve leaflets and thereafter the other of the two valve leaflets; and allowing the clip to move toward its closed configuration to hold the two valve leaflets together.

18. The method of claim 17 wherein positioning the clip comprises pulling the flexible member to pull the two leaflets together.

19. The method of claim 18 wherein the clip second end is provided with a stopper.

20. The method of claim 17 further comprising:

releasably grabbing the needle with a needle holder;

inserting a cannula through an incision in the patient;

advancing the needle holder through the cannula and toward the valve leaflets;

manipulating the needle holder to pass the needle through both valve leaflets;

manipulating the clip to pull the leaflets together and position the clip so as to span the leaflets;

releasing the needle from said needle holder; and detaching the clip from the needle.

* * * * *